United States Patent
Patsalides (10) Patent No.: US 12,285,347 B2
(45) Date of Patent: Apr. 29, 2025

(54) INTRACRANIAL STENT FOR INSERTION INTO THE CEREBRAL VENOUS SINUS SYSTEM AND METHODS OF USE

(71) Applicant: Sonorous NV, Lake Forest, CA (US)

(72) Inventor: Athos Patsalides, New York, NY (US)

(73) Assignee: Sonorous NV, Lake Forest, CA (US)

( * ) Notice: Subject to any disclaimer, the term of this patent is extended or adjusted under 35 U.S.C. 154(b) by 0 days.

(21) Appl. No.: 17/393,120

(22) Filed: Aug. 3, 2021

(65) Prior Publication Data

US 2022/0031488 A1    Feb. 3, 2022

Related U.S. Application Data

(60) Provisional application No. 63/060,218, filed on Aug. 3, 2020.

(51) Int. Cl.
*A61F 2/966* (2013.01)
*A61F 2/90* (2013.01)
A61F 2/95 (2013.01)

(52) U.S. Cl.
CPC ............... *A61F 2/966* (2013.01); *A61F 2/90* (2013.01); *A61F 2002/9528* (2013.01); *A61F 2002/9534* (2013.01); *A61F 2240/002* (2013.01)

(58) Field of Classification Search
CPC .... A61F 2/966; A61F 2/90; A61F 2002/9528; A61F 2002/9534; A61F 2240/002; A61F 2/86
See application file for complete search history.

(56) References Cited

U.S. PATENT DOCUMENTS

| | | |
|---|---|---|
| 7,326,225 B2 | 2/2008 | Ferrera et al. |
| 7,645,275 B2 | 1/2010 | O'Connor et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,197,493 B2 | 6/2012 | Ferrera et al. |
| 8,545,514 B2 | 10/2013 | Ferrera |
| 8,572,262 B2 | 10/2013 | Ensing et al. |
| 8,574,262 B2 | 11/2013 | Ferrera et al. |

(Continued)

FOREIGN PATENT DOCUMENTS

| | | |
|---|---|---|
| EP | 1486186 | 12/2004 |
| WO | WO 2014150288 A2 | 9/2014 |

(Continued)

OTHER PUBLICATIONS

PCT International Search Report and Written Opinion dated Nov. 18, 2021, International Application No. PCT/US2021/044382, pp. 1-8.

(Continued)

*Primary Examiner* — Sarah A Long
(74) *Attorney, Agent, or Firm* — Fish & Richardson P.C.

(57) ABSTRACT

A stent for insertion into an intracranial blood vessel of the cerebral venous sinus system includes a proximal end, a distal end, a body between the proximal end and the distal end, the body comprising a plurality of wires in a closed pattern, wherein the stent is configured for insertion into an intracranial blood vessel of the cerebral venous sinus system. The stent is further capable of being repositioned, retrieved/re-sheathed, and removed for more precise delivery.

19 Claims, 9 Drawing Sheets

(56) References Cited

U.S. PATENT DOCUMENTS

| | | |
|---|---|---|
| 8,585,713 B2 | 11/2013 | Ferrera et al. |
| 8,945,143 B2 | 2/2015 | Ferrera et al. |
| 8,945,172 B2 | 2/2015 | Ferrera et al. |
| 8,998,985 B2 | 4/2015 | Gross et al. |
| 9,198,687 B2 | 12/2015 | Fulkerson et al. |
| 9,220,522 B2 | 12/2015 | Fulkerson et al. |
| 9,320,532 B2 | 4/2016 | Ferrera et al. |
| 9,387,098 B2 | 7/2016 | Ferrera et al. |
| 9,439,791 B2 | 9/2016 | Vong et al. |
| 9,566,071 B2 | 2/2017 | Takahashi et al. |
| 9,566,072 B2 | 2/2017 | Le et al. |
| 9,585,741 B2 | 3/2017 | Ma |
| 9,775,730 B1* | 10/2017 | Walzman ................. A61F 2/86 |
| 9,808,359 B2 | 11/2017 | Ferrera et al. |
| 9,926,680 B2 | 3/2018 | Boasso |
| 10,016,211 B2 | 7/2018 | Ferrera et al. |
| 10,070,878 B2 | 9/2018 | Ma |
| 10,123,803 B2 | 11/2018 | Ferrera et al. |
| 10,143,310 B1 | 12/2018 | Wang |
| 10,182,931 B2 | 1/2019 | Pung et al. |
| 10,322,020 B2 | 6/2019 | Lam et al. |
| 10,335,299 B2 | 7/2019 | Lam et al. |
| 10,342,546 B2 | 7/2019 | Sepetka et al. |
| 10,383,751 B2 | 8/2019 | Ferrera et al. |
| 10,398,877 B2 | 9/2019 | Vitullo et al. |
| 10,617,544 B2 | 4/2020 | Sepetka et al. |
| 10,722,242 B2 | 7/2020 | Le et al. |
| 10,729,447 B2 | 8/2020 | Shimizu et al. |
| 2002/0032459 A1 | 3/2002 | Horzewski et al. |
| 2009/0132024 A1 | 5/2009 | Berkhoff |
| 2010/0174366 A1 | 7/2010 | Avior |
| 2011/0160763 A1 | 6/2011 | Ferrera et al. |
| 2011/0301685 A1 | 12/2011 | Kao |
| 2011/0319917 A1 | 12/2011 | Ferrera et al. |
| 2012/0022576 A1 | 1/2012 | Ferrera et al. |
| 2012/0197285 A1 | 8/2012 | Martin et al. |
| 2013/0030521 A1 | 1/2013 | Nitzan et al. |
| 2013/0304193 A1* | 11/2013 | Osman ................. A61F 2/915 |
| | | 623/1.16 |
| 2014/0058436 A1 | 2/2014 | Rosenbluth et al. |
| 2014/0243882 A1 | 8/2014 | Ma |
| 2014/0309673 A1 | 10/2014 | Dacuycuy et al. |
| 2016/0206323 A1 | 7/2016 | Hebert et al. |
| 2016/0206452 A1 | 7/2016 | Berez et al. |
| 2016/0256255 A9 | 9/2016 | Ma |
| 2016/0354099 A1 | 12/2016 | Turjman et al. |
| 2017/0086992 A1 | 3/2017 | Ferrera et al. |
| 2017/0196717 A1 | 7/2017 | Fulkerson et al. |
| 2018/0250498 A1 | 9/2018 | Stern et al. |
| 2018/0256378 A1* | 9/2018 | Callister ................. A61F 2/915 |
| 2018/0339148 A1 | 11/2018 | Kong |
| 2019/0231302 A1 | 8/2019 | Tieu |
| 2019/0298977 A1 | 10/2019 | Heilman et al. |
| 2019/0364374 A1 | 11/2019 | Jensen et al. |
| 2020/0021929 A1 | 1/2020 | Farrar-Ganes et al. |
| 2020/0069410 A1 | 3/2020 | Amans |
| 2020/0146852 A1 | 5/2020 | Raychev et al. |
| 2020/0368388 A1* | 11/2020 | You ................. A61M 31/002 |
| 2021/0100667 A1 | 4/2021 | Ngo et al. |
| 2021/0137715 A1 | 5/2021 | Ringwala et al. |
| 2021/0205105 A1 | 7/2021 | Stout |
| 2022/0096792 A1 | 3/2022 | Bednarek |
| 2022/0226136 A1 | 7/2022 | Stout |
| 2022/0409239 A1 | 12/2022 | Fischell et al. |
| 2023/0097980 A1* | 3/2023 | Amans ................. A61F 2/90 |
| | | 606/1 |
| 2023/0293283 A1 | 9/2023 | Takahashi et al. |
| 2024/0074879 A1 | 3/2024 | Ferrera et al. |
| 2024/0139471 A1 | 5/2024 | Kessler et al. |
| 2024/0164927 A1 | 5/2024 | Stout |
| 2024/0268976 A1 | 8/2024 | Amans et al. |
| 2024/0366360 A9 | 11/2024 | Takahashi et al. |

FOREIGN PATENT DOCUMENTS

| | | |
|---|---|---|
| WO | WO 2019135220 | 7/2019 |
| WO | WO 2020109979 | 6/2020 |
| WO | WO 2022031730 | 2/2022 |
| WO | WO 2022165166 | 8/2022 |
| WO | WO 2023220571 A1 | 11/2023 |

OTHER PUBLICATIONS

Srikanth R. Boddu et al., "Anatomic measurements of cerebral venous sinuses in idiopathic intracranial hypertension patients," PLoS One 13(6): 2018, pp. 1-10.

B. Schaller, "Physiology of cerebral venous blood flow: from experimental data in animals to normal function in humans," Brain Research Reviews, 46 (2004), pp. 243-260.

Boddu et al., "Resolution of Pulsatile Tinnitus after Venous Sinus Stenting in Patients with Idiopathic Intracranial Hypertension," PLoS One, Oct. 2016, 11(10): e0164466, 13 pages.

Bosstent System Product, Novel Neuro Interventional BosStent System, 17 pages.

Haley et al., A Rational Approach to Meshing Cerebral Venous Geometries for High-Fidelity Computational Fluid Dynamics, 24 pages.

International Preliminary Report on Patentability in International Appln. No. PCT/US2021/044382, mailed on Feb. 16, 2023, 8 pages.

International Search Report and Written Opinion in International Appln. No. PCT/US2022/014297, mailed on May 18, 2022, 10 pages.

Mayo Foundation for Medical Education and Research (MFMER), "Tinnitus symptoms & causes," Mayo Clinic, Mar. 5, 2019, 1998-2020, CON-20118272, 8 pages.

Mayo Foundation for Medical Education and Research, "Tinnitus diagnosis & treatment," Mayo Clinic, available on or before Jun. 14, 2019, via Internet Archive: Wayback Machine URL <https://www.mayoclinic.org/diseases-conditions/tinnitus/diagnosis-treatment/drc-20350162>, URL<https://www.mayoclinic.org/diseases-conditions/tinnitus/diagnosis-treatment/drc-20350162>, 7 pages.

Park et al., "Awake embolization of sigmoid sinus diverticulum causing pulsatile tinnitus: simultaneous confirmative diagnosis and treatment," Interventional Neuroradiology, Oct. 2011, 17:376-379.

The Pulse Clinic: Advanced Pulsatile Tinnitus & Intracranial Hypertension Assessment; 36 pages.

Venous Stenting Landscape, 22 pages.

fwmetals.com [online], "Composite Materials: DFT® wire," retrieved on Apr. 22, 2024, retrieved from URL<https://www.fwmetals.com/products/composites-dft-wire/dft-wire/>, 1 page.

steegerusa.com [online], "Catheter Braid Patterns for Medical Braiding," retrieved on Apr. 22, 2024, retrieved from URL<https://steegerusa.com/typical-braid-patterns-for-medical-braiding/#:~:text=Braid%20density%2C%20also%20known%20as,pushability%2C%20torque%20requirements%20and%20more>, 8 pages.

Sundararajan et al., "Dural Venous Sinus Stenosis: Why Distinguishing Intrinsic-versus-Extrinsic Stenosis Matters," AJNR Am J Neuroradiol, Feb. 2021, available online Jan. 7, 2021, 42(2):288-296.

Extended European Search Report in European Appln. No. 21854427.8, mailed on Jul. 30, 2024, 8 pages.

Office Action in European Appln. No. 21854427.8, mailed on Feb. 14, 2025, 6 pages.

* cited by examiner

INTRACRANIAL STENT FOR INSERTION INTO THE CEREBRAL VENOUS SINUS SYSTEM AND METHODS OF USE

FIELD OF THE DISCLOSURE

The present disclosure relates to stents suitable for treating conditions or diseases in the intracranial/cerebral veins. In particular, the present disclosure relates to expandable, retrievable, and re-sheathable structures configured to reduce restenosis and thrombus formation in the intracranial/cerebral veins.

BACKGROUND

Generally, stents are commonly indicated for a variety of intravascular and non-vascular applications, including restoration and/or maintenance of patency within a patient's vessel. Stents are also used to reduce restenosis of a blood vessel post-dilation, thereby ensuring adequate blood flow through the vessel.

A new procedure has been carried out that involves placing a stent in the cerebral venous sinuses of patients to ameliorate a collapse of and/or a stenosis in the sigmoid and/or transverse sinus and/or superior sagittal sinus and to restore blood flow out of the brain. The cerebral venous sinus system (also known as dural venous sinus system) includes the large veins of the brain, namely the superior sagittal venous sinus, the transverse venous sinus, the sigmoid venous sinus and the straight venous sinus. The transverse and sigmoid venous sinuses are collectively called the "lateral" venous sinus. The cerebral venous sinuses receive blood from tributaries called cortical veins that drain in the side wall of the venous sinuses.

The stent used in the new procedure typically is the same stent used for procedures in other parts of the body, such as the carotid/peripheral arteries or even the biliary system. The cerebral venous sinus structure, for instance, does not resemble any vein or arteries of other parts of the body. Instead, the venous sinus is a void created where the dura joins and forms a cavity (i.e., sinus) primarily along the inside of the skull. In this regard, the dura has no smooth muscle cell lining and is inelastic when compared to veins and arteries. In addition, the cerebral venous sinus system does not have a cylindrical shape, and is instead ovoid or even triangular.

Another limitation of the current stent systems used in the cerebral venous sinuses is that the length of cerebral venous sinus stenosis often exceeds the length of existing stents, often leading to placement of more than one stents adjacent to each other. A stent specifically designed for this anatomic location needs to have longer length in order to treat the entire length of the stenosis.

Current stent designs have struts designed to expand a stiff calcified atherosclerotic plaque. These struts are numerous and thick, leading to increased risk of obstructing flow from a tributary vein into the cerebral venous sinus.

The first stent that was designed for the intracranial veins (River Stent, Serenity Medical, Inc.) is being currently evaluated in clinical trials. The River stent is an open cell, self-expandable, Nitinol stent delivered over 0.014 wire. However, even this stent experiences some shortcomings. Namely, once this stent is positioned in the desired location, it cannot be repositioned, retrieved/re-sheathed, or removed.

There is therefore a need for a stent that is capable of being inserted into the cerebral venous sinus system and that can also be repositioned, retrieved, or removed to allow for more precise delivery. This and other benefits the present disclosure provides.

SUMMARY

There is a need for developing a stent that is capable of being inserted into cerebral venous sinus system. The present disclosure is directed toward further solutions to address this need, in addition to having other desirable characteristics. For example, the stent of the present disclosure can also be repositioned, retrieved, or removed to allow for more precise delivery into the cerebral venous sinus system than previously known stents.

According to some embodiments of the present disclosure, a stent includes a proximal end, a distal end, a body between the proximal end and the distal end, the body comprising a plurality of wires interbraided in a closed cell pattern, wherein the stent is configured for insertion into an intracranial target blood vessel.

The stent is self-expandable or self-expanding, meaning the stent is constrained within a sheath of a delivery catheter until positioned and deployed in a desired location in the target blood vessel.

According to aspects of the present disclosure, the stent can be reconstrained and retrieved within the delivery system and repositioned in the blood vessel even after partial deployment.

According to aspects of the present disclosure, if the stent is partially deployed, it can be retrieved from the blood vessel after an interval of time.

According to aspects of the present disclosure, the stent can be re-sheathed after it has begun expanding.

According to aspects of the present disclosure, the body has a diameter between about 6 mm and 10 mm.

According to aspects of the present disclosure, the body has a length between about 40 mm and about 80 mm.

According to aspects of the present disclosure, the stent is capable of transitioning between a collapsed configuration and an expanded configuration.

According to some embodiments of the present disclosure, the body is formed of a combination of platinum, cobalt, chromium, stainless steel, nickel and titanium alloy.

According to some aspects of the present disclosure, the target blood vessel for stent deployment can include at least one, or any one of, the cerebral venous sinus, the superior sagittal venous sinus, transverse venous sinus, sigmoid venous sinus and straight venous sinus.

According to aspects of the present disclosure, stent is used to treat any one of a variety of medical conditions including idiopathic intracranial hypertension, pulsatile tinnitus, cerebral venous insufficiency, intracranial venous thrombosis, and intracranial venous stenosis, which venous stenosis includes compression from tumor, compression from brain parenchyma, compression from arachnoid granulation, and compression from blood clot (thrombus).

BRIEF DESCRIPTION OF THE DRAWINGS

These and other characteristics of the present disclosure will be more fully understood by reference to the following detailed description in conjunction with the attached drawings, in which:

FIG. 3A and FIG. 3B illustrate an exemplary stent delivery system, in accordance with an embodiment of the present disclosure.

FIG. 5A-FIG. 5C are schematic isometric views illustrating the basic structure of a stent of the present disclosure in use.

DETAILED DESCRIPTION OF EMBODIMENTS

An illustrative embodiment of the present disclosure relates to a stent that is capable of being inserted into the cerebral venous sinuses and that is also capable of being repositioned, retrieved, or removed to allow for more precise delivery.

FIG. 1 through FIG. 4A-FIG. 4C, wherein like parts are designated by like reference numerals throughout, illustrate an example embodiment or embodiments of stent that is capable for being inserted into the cerebral venous sinuses, according to the present disclosure. Although the present disclosure will be described with reference to the example embodiment or embodiments illustrated in the figures, it should be understood that many alternative forms can embody the present disclosure. One of skill in the art will additionally appreciate different ways to alter the parameters of the embodiment(s) disclosed, such as the size, shape, or type of elements or materials, in a manner still in keeping with the spirit and scope of the present disclosure.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property can include additional elements not having that property. As referred to herein, the terms "proximal" and "distal" are in relation to the delivery handle of the stent delivery system (also referred to as a catheter). For example, the distal end 104 of the stent 100 and the catheter is the end that is inserted first into a body of a patient and the proximal end 106 is opposite the distal end 104.

Figure 1:
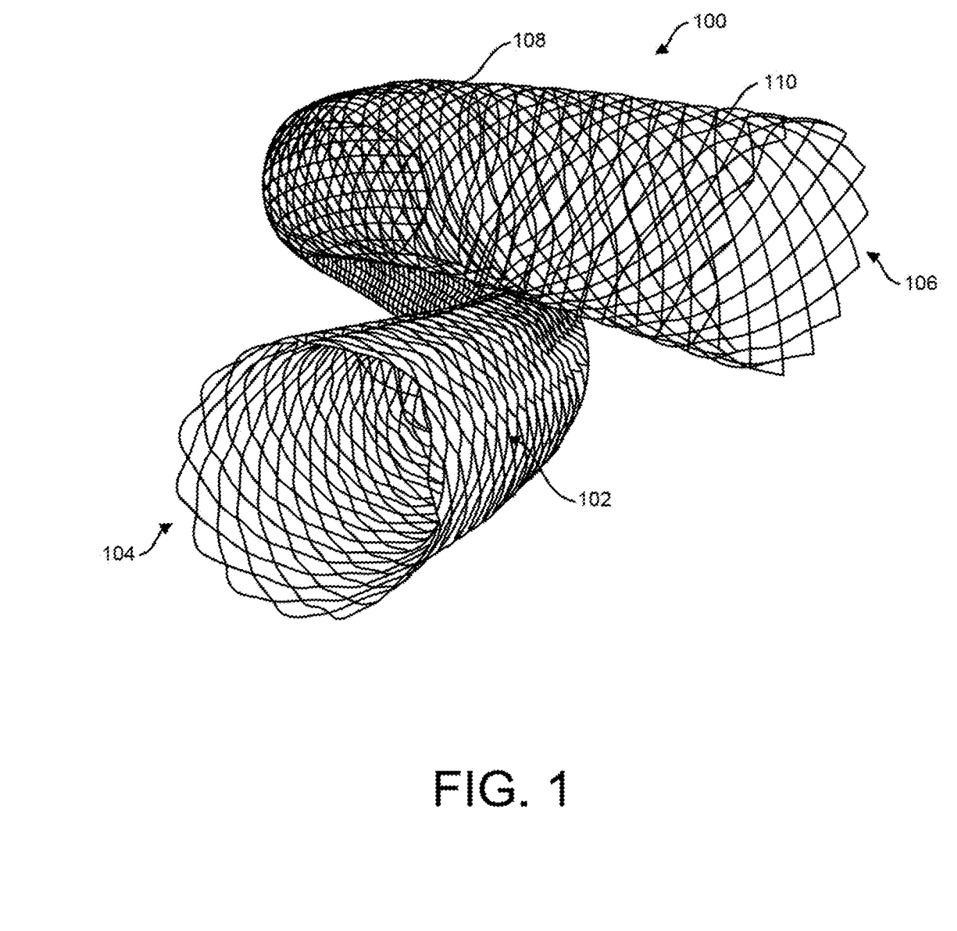
FIG. 1 is an exemplary stent in accordance with an embodiment of the present disclosure.
Figure 2:
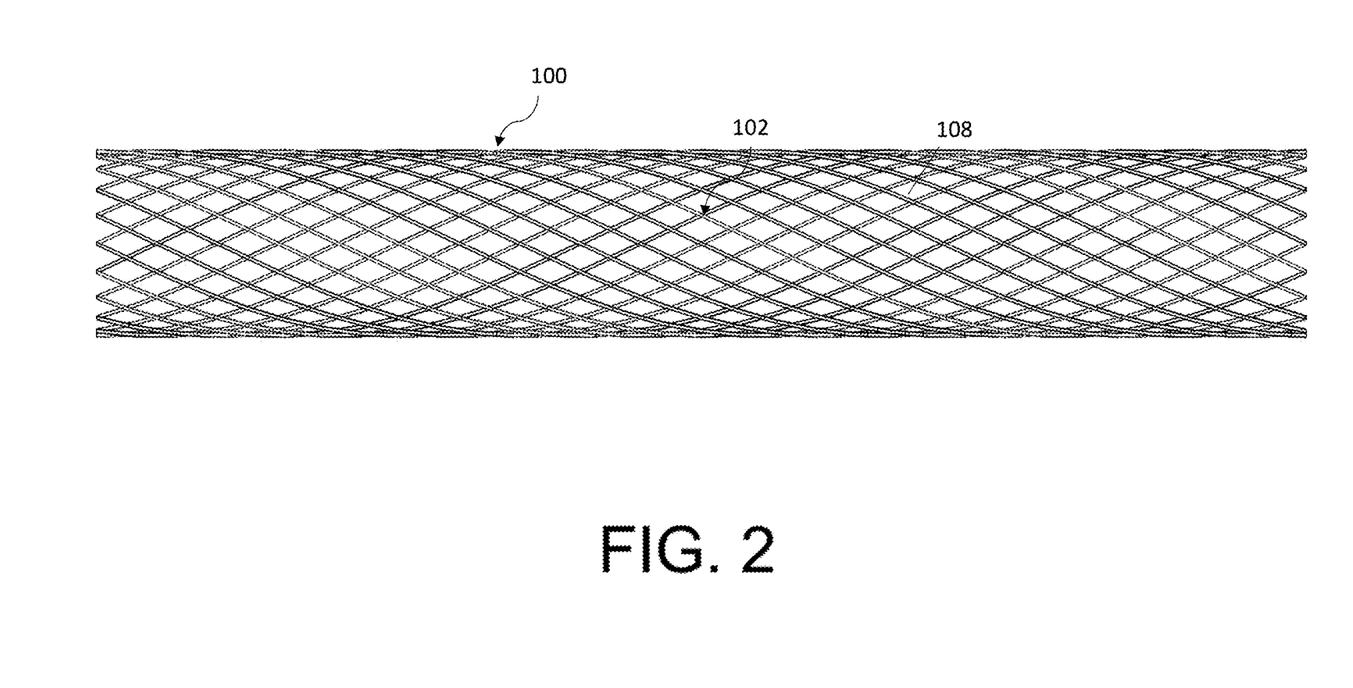
FIG. 2 is an exemplary stent in accordance with an embodiment of the present disclosure.

FIG. 1 and FIG. 2 illustrate an exemplary stent 100 in accordance with various embodiments of the present disclosure. The stent 100 is shown in an expanded configuration. Stent 100 comprises a tubular flexible body 102 having a distal end 104 and a proximal end 106. Stent 100 further comprises a web structure 108 that is configured to allow the stent 100 to expand from a contracted delivery configuration to an expanded deployed configuration.

In an embodiment, the web structure 108 can have a braided or closed design. As shown in FIG. 1 and FIG. 2, the stent 100 is formed by having a plurality of elongate wires 110 formed into the web structure 108. The elongate wires 110 traverse the length of the stent 100 in a direction traverse to the longitudinal length of the stent 100. The elongate wires 110 can be formed into the web structure 108 by braiding the wires 110, winding the wires 110, knitting the wires 110, and combinations thereof. In one embodiment, the wires 110 are laser-cut in a closed cell pattern to form the web structure 108. The diameter of the struts in the web structure 108 will be carefully optimized to modulate the radial outward force across the entire length of the stent. The diameter of the struts will vary from about 0.1 mm to about 1 mm. As used herein, the term "about" or "approximately" refers to a variation of 10% from the indicated values (e.g., 0.1 mm, 1 mm, etc.), or in case of a range of values, means a 10% variation from both the lower and upper limits of such ranges. For instance, "about 1 mm" refers to a range of between 0.9 mm and 1.1 mm.

In accordance with an embodiment of the present disclosure, the web structure 108 is configured to allow the stent 100 to self-expand and contract as many times as necessary until the stent 100 reaches the correct location and can be deployed and secured. A stent that is able to contract after it has expanded to a certain point and move back into its delivery system is referred to as a stent that is "retrievable" or "re-sheatheable." In an embodiment, the stent 100 is capable of being retrieved or re-sheathed even when the stent 100 is between about seventy percent (70%) and eighty-five percent (85%) expanded. In an embodiment, the stent 100 is capable of being retrieved or re-sheathed even when the stent 100 is about eighty-five percent (85%) expanded. In an embodiment, the stent 100 is capable of being retrieved or re-sheathed even when the stent 100 is about eighty percent (80%) expanded. In an embodiment, the stent 100 is capable of being retrieved or re-sheathed even when the stent 100 is about seventy-five percent (75%) expanded. In an embodiment, the stent 100 is capable of being retrieved or re-sheathed even when the stent 100 is about seventy percent (70%) expanded. By being retrievable or re-sheathable, the stent 100 of the present disclosure is capable of being repositioned multiple times before being secured into place. This allows the stent 100 to be positioned, repositioned, and even removed until the desired location is found. In this way, the stent 100 of the present disclosure allows for more precise delivery of the stent 100.

Stents are typically implemented in either a closed cell pattern, an open cell pattern, or a braided cell pattern. A stent with a "closed cell pattern" has each peak and valley of each strut segment connected to a peak or valley of an adjacent strut segment, with the exception of the strut segments on the proximal and distal ends. Stents with an "open cell pattern," on the other hand, have some peaks and/or valleys that are not connected to peaks and/or valleys of adjacent strut segments. Stents with braided patterns include a one over and one under pattern, but other patterns can suitably be used, knitting wires or wire filaments into a braided loop, the pattern of which loops are formed from a relaxed state, where each row of loops is axially and independently of the rows on either side. In an embodiment, the stent 100 can have a closed cell pattern design, for example, to allow the stent 100 to expand and collapse multiple times before being secured. Moreover, a closed cell pattern stent structure has an enhanced ability to expand and conform to a non-circular cavity wall, such as the sinuses, when compared to an open cell pattern structure. For example, the individual segments of a closed cell pattern stent have more flexibility than the segments of an open cell pattern stent. Such flexibility beneficially increases a clinician's ability to guide the stent to a target site within a patient's vessel. Accordingly, the closed cell pattern segments are better suited for conforming to irregularities of a non-circular cavity.

Furthermore, stents of the present invention preferably exhibit high radial stiffness in the deployed configuration. Implanted stents therefore are capable of withstanding compressive forces applied by a vessel wall, thereby alleviating stenosis and maintaining vessel patency. The web structure 108 of the present disclosure provides the desired combination of flexibility in the delivery configuration to allow for safe navigation and radial stiffness in the deployed configuration to allow for excellent apposition to the vessel wall. In addition, the flexibility of the web structure 108 of the present disclosure allows the stent 100 to conform to the anatomy of the intracranial veins.

The stent 100 of the present disclosure can be sized to cover the anatomy of the intracranial veins. For example, depending on the area of need, the length of the stent 100 can be between about 40 mm to about 80 mm long. In an embodiment, the length of the stent 100 is between about 40 mm to about 45 mm. In an embodiment, the length of the stent 100 is between about 45 mm to about 50 mm. In an embodiment, the length of the stent 100 is between about 50 mm to about 55 mm. In an embodiment, the length of the stent 100 is between about 55 mm to about 60 mm. In an embodiment, the length of the stent 100 is between about 60 mm to about 65 mm. In an embodiment, the length of the stent 100 is between about 65 mm to about 70 mm. In an embodiment, the length of the stent 100 is between about 70 mm to about 75 mm. In an embodiment, the length of the stent 100 is between about 75 mm to about 80 mm. As used herein, the term "about" or "approximately" refers to a variation of 10% from the indicated values (e.g., 40 mm, 45 mm, 50 mm, etc.), or in case of a range of values, means a 10% variation from both the lower and upper limits of such ranges. For instance, "about 40 mm" refers to a range of between 36 mm and 44 mm.

Depending on the area of treatment, the diameter of the stent 100 can be between about 6 mm to about 10 mm. In an embodiment, the diameter of the stent 100 is between about 6 mm and about 7 mm. In an embodiment, the diameter of the stent 100 is between about 7 mm and about 8 mm. In an embodiment, the diameter of the stent 100 is between about 8 mm and about 9 mm. In an embodiment, the diameter of the stent 100 is between about 9 mm and about 10 mm. The diameter can be the same from one end to the other end or the diameter can be tapered. In one embodiment, for example, the stent 100 can be 7 mm at one end and gradually increase to 9 mm at the other end.

The stent 100 of the present disclosure can be made of wires comprising a combination of suitable materials, including platinum, cobalt, chromium, stainless steel, nickel and titanium. Since the stent 100 of the present disclosure is self-expanding and also retrievable/re-sheathable, the web structure 108 in an embodiment is fabricated from an elastic material. In accordance with further embodiments of the present disclosure, stent 100 is fabricated from biocompatible and/or biodegradable materials. Biocompatible material can comprise a biocompatible polymer, for example, a modified thermoplastic Polyurethane, Polyethylene Terephthalate, Polyethylene Tetraphthalate, expanded Polytetrafluoroethylene, Polypropylene, Polyester, Nylon, Polyethylene, Polyurethane, or combinations thereof.

In some embodiment, stent 100 can contain an external coating or attached active groups C configured for localized delivery of radiation, gene therapy, medicaments, thrombin inhibitors, or other therapeutic agents. For example, stent 100 can be coated with therapeutic agents to help prevent or delay thrombus formation or restenosis within a vessel. Coatings or active groups C can, in an embodiment, be absorbed or adsorbed onto the surface, can be attached physically, chemically, biologically, electrostatically, covalently, or hydrophobically, or can be bonded to the surface through VanderWaal's forces, or combinations thereof, using a variety of techniques that are well-known in the art.

Figure 3A:
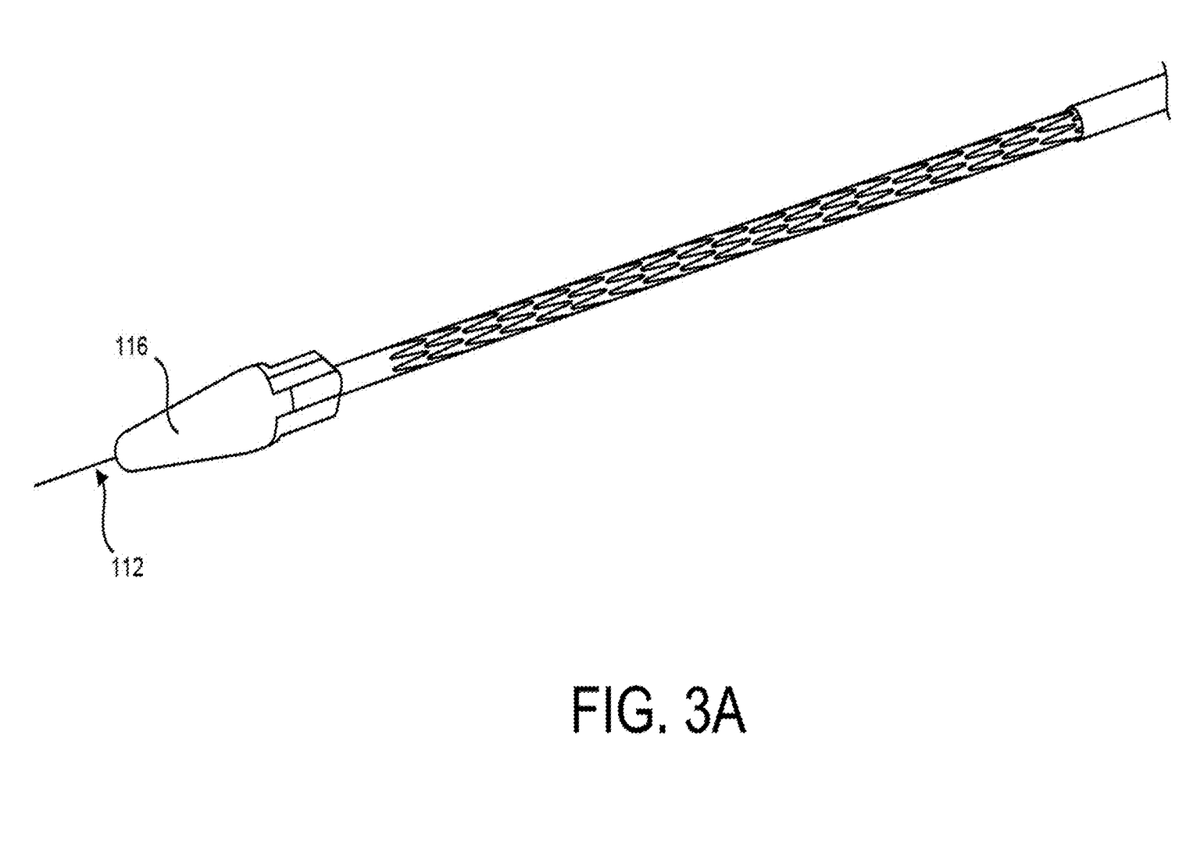
FIG. 3A is a schematic view illustrating the stent in a closed position.
Figure 3B:
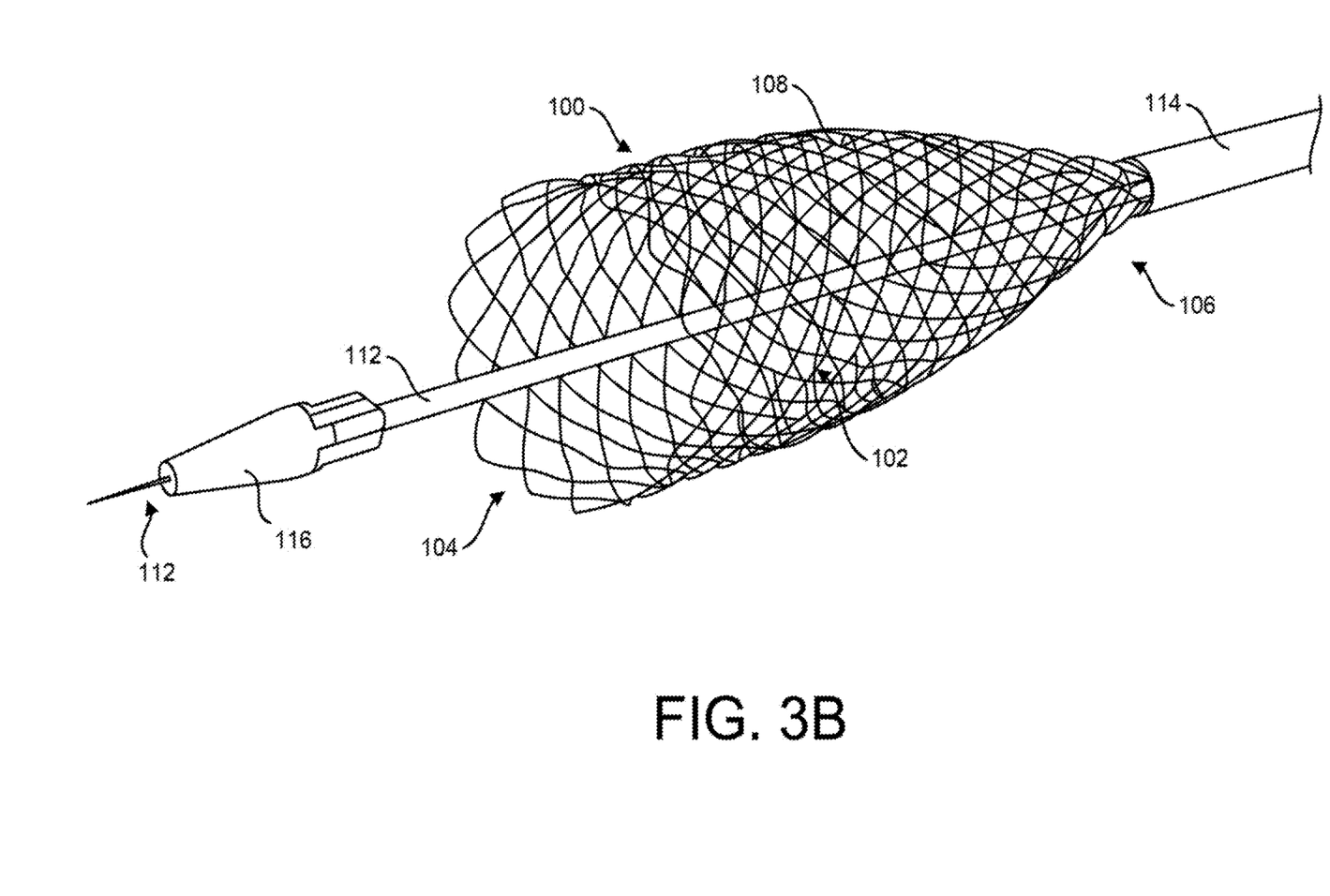
FIG. 3B is a schematic view illustrating the stent in a deployed position.

Referring now to FIG. 3A and FIG. 3B, stent 100 is depicted in operation. Using known methods, stent 100 can be delivered over a guide wire 112 via a small incision basilic, femoral, or internal jugular veins and the use of fluoroscopic guidance. To deliver the stent 100 to its desired location, the stent 100, in a collapsed configuration as shown in FIG. 3A, is first inserted into a lumen 114, then guided through the veins with the help of the guide wire 112. The guide wire 112 can be any known guide wire used in the art that is sufficiently sized to navigate through a venous sinus. In one embodiment, the guide wire 112 may be about 0.014 mm in diameter. Once at the desired location, the lumen 114 can be pulled back to expose the stent 100 as shown in FIG. 3B. Upon exposure, the stent self-expands and secures itself to the surrounding vessel walls.

To assist in delivering stent 100 to its desired location, stent 100 may have a tip 116 at its distal end 104. This will allow for atraumatic advancement of the stent through a blood vessel or narrowed venous sinus, especially in cases where there is an abnormality within the lumen of the venous sinus (clot, arachnoid granulation). The tip 116 may be shaped as a cone, a wedge, or other similar shape with a tapered end that allows it to maneuver through the venous sinus. The tip 116 may be approximately 20 mm in length but can also be between approximately 10 mm in length to approximately 25 mm in length. The diameter of tip 116 can be same from one end to the other end or the diameter can be tapered. In one embodiment, for example, the diameter of tip 116 can be 7 mm in one end and gradually increase to 9 mm at the other end.

If necessary, the stent 100 can be retrieved or re-sheathed after it has been deployed. For instance, if the user (e.g., physician) determines that the stent 100 is not in the proper location after the stent 100 has begun to self-expand, the user can still retrieve the stent by causing the stent 100 to collapse back into the lumen 114. In an embodiment, the stent 100 can still be retrieved or re-sheathed with the lumen 114, even when the stent 100 is about eighty percent expanded.

Figure 4A:
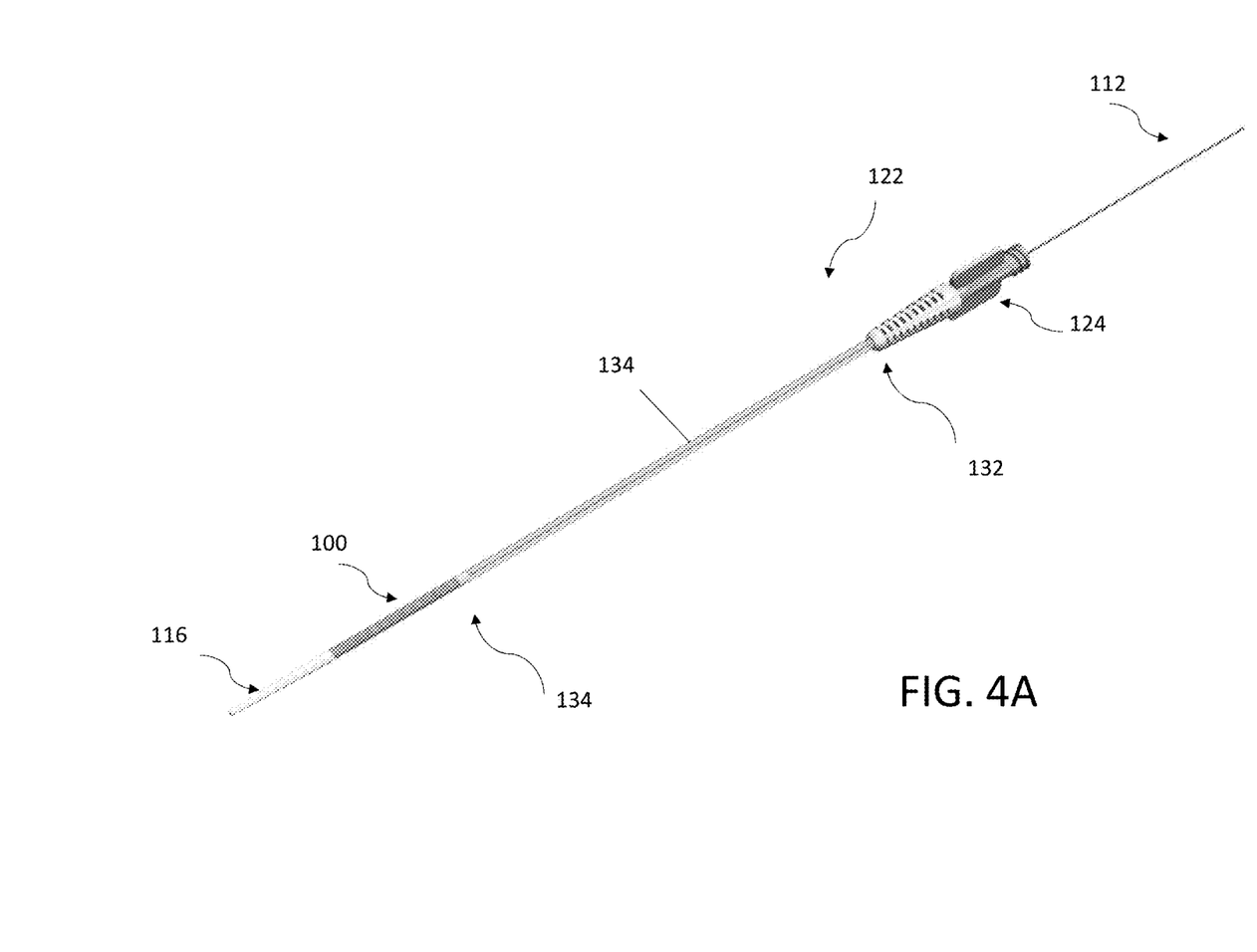
FIG. 4A-FIG. 4C illustrate an exemplary stent delivery system, in accordance with an embodiment of the present disclosure.
Figure 4B:
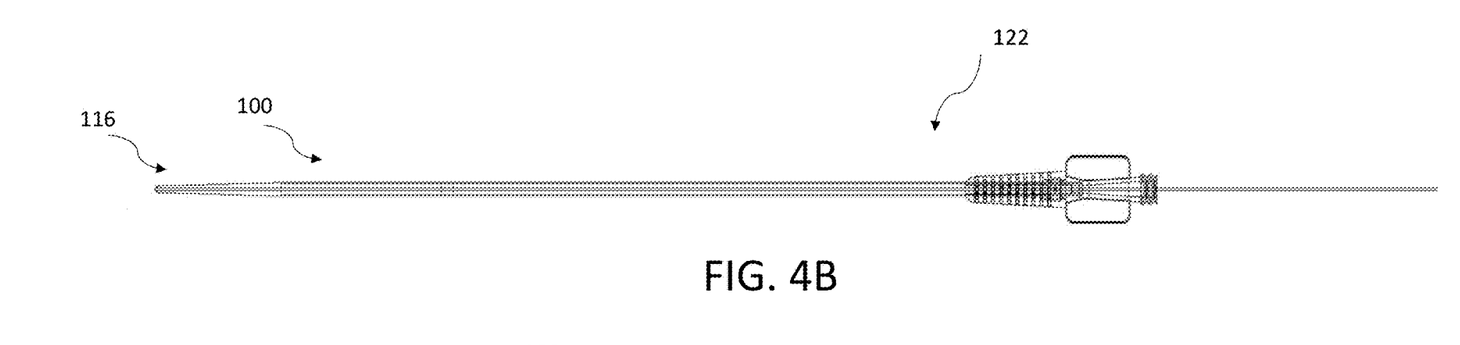
Figure 4C:
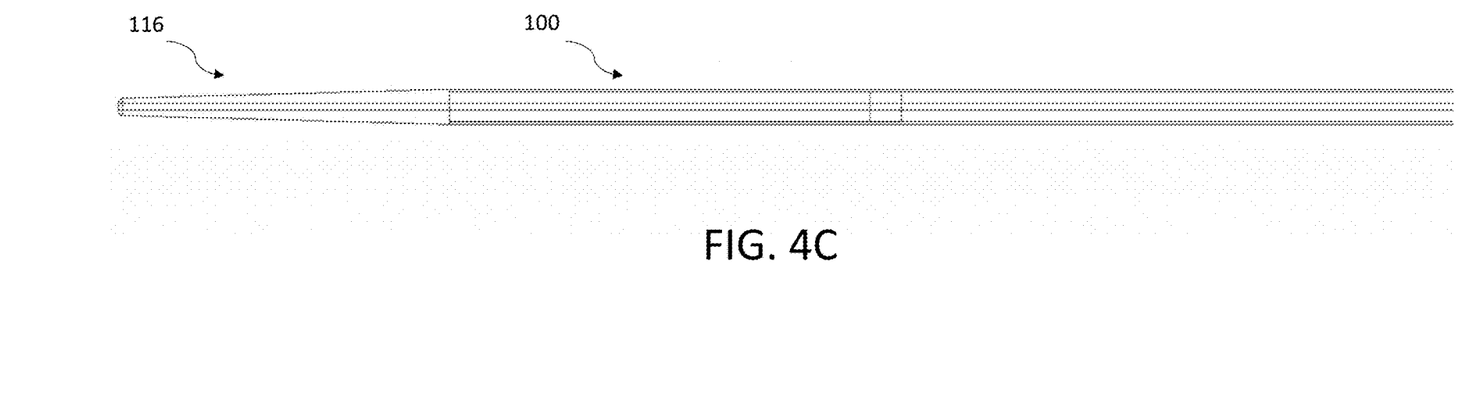

FIG. 4A, FIG. 4B, and FIG. 4C illustrate an implant delivery system 120 in accordance with an embodiment of the present disclosure. In an embodiment, the implant delivery system 120 may include stent 100, a catheter 122 with hub 124 and guide wire 112 extending through catheter 122 and hub 124. In an embodiment, catheter 122 may have a distal end 130, a proximal end 132, and a lumen 134 extending between the distal end 130 and the proximal end 132. Catheter 122 is relatively flexible, may be comprised of a polymeric material such as nylon or PEBAX, and may range in length from 60 cm to 300 cm. Guide wire 112 diameter may be large enough to allow passage of guidewires ranging in diameter from 0.009 mm to 0.038 mm. Hub 124 is removably attached to the proximal end 132 of catheter 122, is adapted to reversibly connect to other medical devices, and may be comprised of polycarbonate or any other suitable material. At the distal end 130 of catheter 122 is stent 100. At distal end 104 of stent 100 is tip 116.

An exemplary method of using a stent 100 with implant delivery system 120 is now described. A guide wire 112 is advance into a patient's peripheral vein (femoral vein, basilic vein, internal jugular vein) using known techniques, through a patient's vessel and to a treatment site. Stent 100 is loaded onto implant delivery system 120 in a collapsed position and introduced over the guidewire into the patient's vessel. The stent 100 and implant delivery system 120 combination is advanced over the guidewire 112 and through the patient's vessel until stent 100 is located at a treatment site, for example within a stenosis in the cerebral venous sinus system. Stent 100 is deployed by releasing the stent 100 thereby allowing stent 100 to self-expand. If necessary to reposition stent 100, stent 100 may be retrieved or re-sheathed by collapsing the stent 100 within the catheter 122. Once the stent 100 is deployed, catheter 122 is then withdrawn through the patient's vessel and out of the patient's body.

Figure 5A:
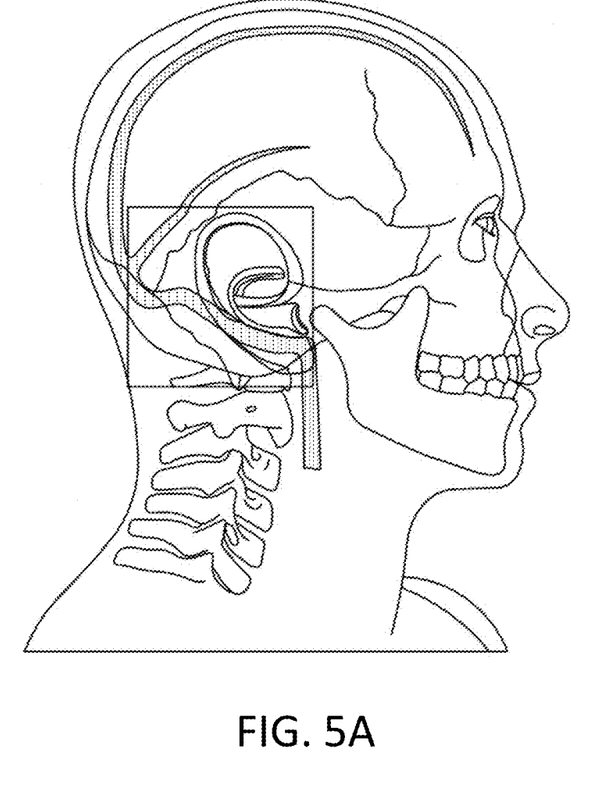
FIG. 5A is a schematic isometric view illustrating the lateral venous sinus in the brain.
Figure 5B:
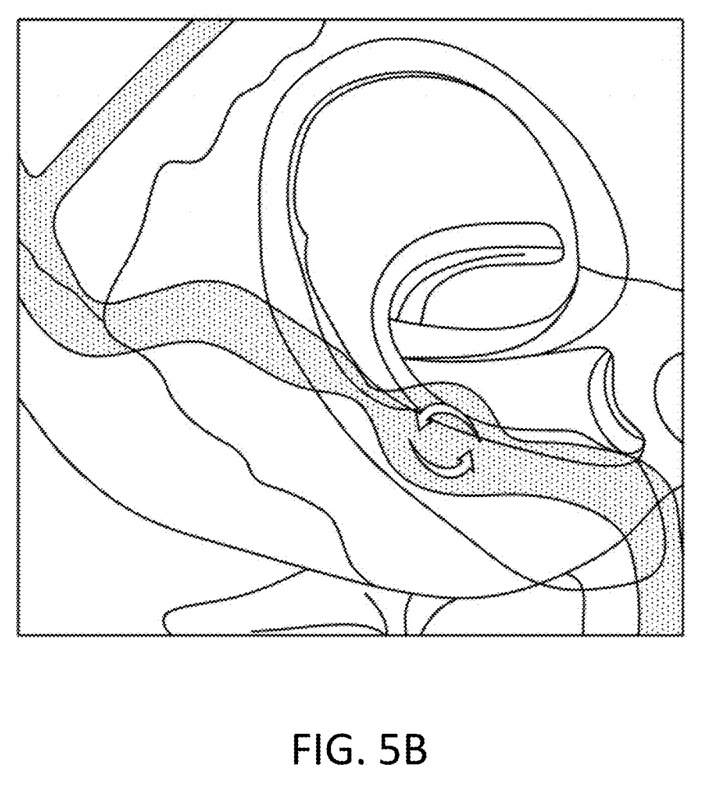
FIG. 5B is a schematic isometric view illustrating a close-up of the lateral venous sinus in the brain.
Figure 5C:
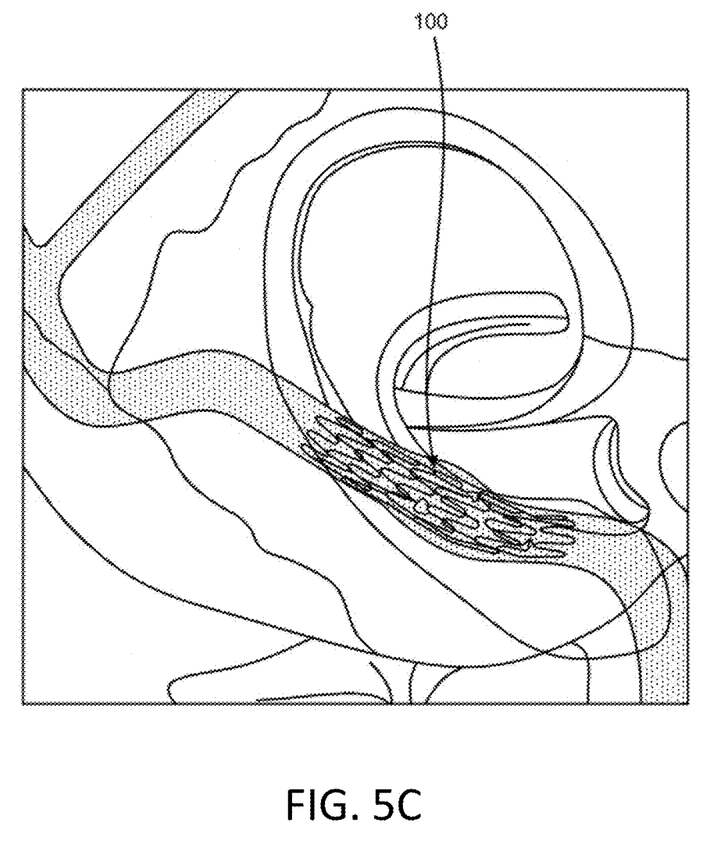
FIG. 5C is a schematic isometric view illustrating an exemplary stent in accordance with an embodiment of the present disclosure secured in the lateral venous sinus in the brain.

Referring to FIG. 5A, FIG. 5B, and FIG. 5C, the stent 100 is shown in use in an intracranial vessel. In operation, the stent is shown secured in the lateral venous sinus which is located within the brain as depicted in FIG. 5C.

With any embodiment, the stent 100 can be inserted into an intracranial vessel which includes, without limitation, the dural venous sinuses (the superior sagittal sinus, transverse sinus, sigmoid sinus, the straight sinus).

With any embodiment, the stent 100 can be used for a number of purposes including to maintain patency of a cerebral venous sinus. Medical conditions that are suited to be treated using the stent 100 of the present disclosure include, without limitation, idiopathic intracranial hypertension, pulsatile tinnitus, cerebral venous insufficiency, intracranial venous thrombosis, and intracranial venous stenosis, including compression from tumor, compression from brain parenchyma, compression from arachnoid granulation, and thrombus.

The stent 100 of the present disclosure provides several notable advantages over stents currently used. First, the stent 100 is specifically designed for use in cerebral venous sinuses rather than for other parts of the body such as the carotid/peripheral arteries. As such, the stent 100 has enhanced conformability to the anatomy of cerebral venous sinuses as compared to stents that were not designed for use in this region. In addition, the stent 100 of the present disclosure is retrievable and re-sheathable which allow it to be positioned, repositioned, and removed prior to being secured. This enhances the ability of the stent 100 to be precisely delivered to its desired location.

Other notable advantages of the stent 100 of the present disclosure include its flexibility to allow for safe navigation through the intracranial veins, its ability to secure itself to the vessel walls, and its ability to alleviate stenosis and restore patency in the veins. These features of the stent 100 are in part due to the unique combination of materials that provide the stent 100 with the required flexibility, stability, and strength.

To treat different conditions in different vessels, the stent 100 of the present disclosure can be customized. In an embodiment, the stent 100 of the present disclosure can have customized, variable zones of chronic outward force that mimic the compliance and adapt to the anatomy of the cerebral venous sinuses (e.g., target vessel). This means that the stent 100 may be stiffer or firmer in some areas and not in others. The stiffer sections can help open, and keep open, those areas of the vessel that are more difficult to open. In one embodiment, the stent 100 may be stiffer in the middle.

In another embodiment. the stent can have customized, variable cell size to adapt to the non-cylindrical shape of cerebral venous sinuses (e.g., target vessel) and achieve excellent apposition to the wall of the cerebral venous sinus. This means that certain sections of the stent 100 may have different spacing between the cells to help conform to the shape of the vessel. This allows the stent 100 of the present disclosure to be used to treat various conditions in different vessels.

In another embodiment, the stent can have customized, variable cell size to prevent obstruction of flow from a tributary vein into the cerebral venous sinus.

Numerous modifications and alternative embodiments of the present disclosure will be apparent to those skilled in the art in view of the foregoing description. Accordingly, this description is to be construed as illustrative only and is for the purpose of teaching those skilled in the art the best mode for carrying out the present disclosure. Details of the structure can vary substantially without departing from the spirit of the present disclosure, and exclusive use of all modifications that come within the scope of the appended claims is reserved. Within this specification embodiments have been described in a way which enables a clear and concise specification to be written, but it is intended and will be appreciated that embodiments can be variously combined or separated without parting from the disclosure. It is intended that the present disclosure be limited only to the extent required by the appended claims and the applicable rules of law.

It is also to be understood that the following claims are to cover all generic and specific features of the disclosure described herein, and all statements of the scope of the disclosure which, as a matter of language, might be said to fall therebetween.

What is claimed is:

1. A stent for permanent implantation into a cerebral venous sinus having a stenosis, comprising:
 a proximal end, a distal end, and
 a tubular flexible body of braided wire providing a closed cell pattern having a variable cell size, between the proximal end and the distal end, wherein the tubular flexible body has the same diameter at the proximal end and the distal end of the stent, and a length of between about 60 mm and about 80 mm; wherein the stent is configured for insertion and permanent implantation into a cerebral venous sinus, the stent being constrained within a lumen of a delivery catheter until the stent is positioned and deployed in the cerebral venous sinus wherein the stent self-expands to open the stenosis after being deployed, and wherein the stent has customized, variable zones of chronic outward force and is configured to secure itself to the surrounding venous sinus walls to be retrievable or re-sheathable, and to be permanently implanted in a desired location in the cerebral venous sinus.

2. The stent of claim 1, wherein the stent is configured to be repositionable in the cerebral venous sinus after deployment.

3. The stent of claim 1, wherein the stent can be retrieved after it has begun to expand.

4. The stent of claim 1, wherein the stent can be re-sheathed within the lumen of the delivery catheter after the stent has begun to expand.

5. The stent of claim 1, wherein the stent is capable of transitioning between a collapsed configuration and an expanded configuration.

6. The stent of claim 1, wherein the cerebral venous sinus is selected from the group consisting of the superior sagittal venous sinus, the transverse venous sinus, the sigmoid venous sinus, and the straight venous sinus.

7. The stent of claim 1, wherein the stent is used to treat a medical condition selected from the group consisting of idiopathic intracranial hypertension, pulsatile tinnitus, cerebral venous insufficiency, intracranial venous thrombosis, and intracranial venous stenosis.

8. The stent of claim 7, wherein intracranial venous stenosis comprises a medical condition resulting from compression from tumor, compression from brain parenchyma, compression from arachnoid granulation, or thrombus.

9. The stent of claim 7, wherein the medical condition is pulsatile tinnitus.

10. The stent of claim 1, wherein the stent can have customized, variable cell size to adapt to a non-cylindrical shape of the cerebral venous sinus.

11. The stent of claim 1, wherein the stent can have customized, variable cell size to prevent obstruction of flow from a tributary vein into the cerebral venous sinus.

12. The stent of claim 1, wherein the stent further comprises a coating of one or more therapeutic agents.

13. The stent of claim 1 wherein the stent is formed of struts having a diameter adjusted to provide radial stiffness in a deployed condition to enable apposition to a vessel wall.

14. The stent of claim 13 wherein the stent is capable of being retrieved or re-sheathed even when the stent is between about seventy and eighty-five percent expanded.

15. An intracranial implant delivery system for implanting a stent into a cerebral venous sinus, comprising:
   a catheter comprising a distal end, a proximal end, and a lumen extending between the distal end and the proximal end;
   a tip located at the distal end of the catheter; and a stent comprising:
   a proximal end, a distal end, and
   a tubular flexible body of braided wire, providing a closed cell pattern and variable cell size, between the proximal end and the distal end of the stent wherein the tubular flexible body has the same diameter of between about 6 mm and 10 mm at the proximal end and the distal end of the stent, and a length of between about 60 mm and about 80 mm and wherein the stent has customized, variable zones of chronic outward force and is configured for insertion into a cerebral venous sinus to alleviate a stenosis, the stent being constrained within a lumen of a delivery catheter until the stent is positioned and deployed in the cerebral venous sinus, and wherein the stent is configured to be re-sheathable, to expand after deployment, to alleviate a stenosis in the venous sinus by forcing a narrowed segment of the vein to expand, and to secure itself to surrounding venous sinus walls and to be implanted in a desired location in the cerebral venous sinus.

16. The system of claim 15, wherein the stent can have customized, variable zones of chronic outward force that mimic the compliance and adapt to the anatomy of the cerebral venous sinus.

17. The system of claim 15, wherein the stent can have customized, variable cell size to adapt to a non-cylindrical shape of the cerebral venous sinus.

18. The system of claim 15, wherein the stent can have customized, variable cell size to prevent obstruction of flow from a tributary vein into the cerebral venous sinus.

19. The system of claim 15, wherein the stent further comprises a coating of one or more therapeutic agents.

* * * * *